United States Patent [19]

Shaw

[11] 4,259,953

[45] Apr. 7, 1981

[54] APPARATUS FOR DISPENSING A LIQUID EYEWASH

[76] Inventor: Anthony Shaw, 1 Marlborough St., Upper Hutt, New Zealand

[21] Appl. No.: 67,945

[22] Filed: Aug. 20, 1979

[51] Int. Cl.[3] .................... A61M 1/00

[52] U.S. Cl. .................... 128/233

[58] Field of Search .................... 128/233, 225, 200.14, 128/249

[56] References Cited

U.S. PATENT DOCUMENTS

| | | | |
|---|---|---|---|
| 3,439,674 | 4/1969 | Lelicoff | 128/233 |
| 3,934,585 | 1/1976 | Maurice | 128/233 X |

*Primary Examiner*—John D. Yasko

*Attorney, Agent, or Firm*—Bucknam and Archer

[57] ABSTRACT

By this invention there is provided an apparatus for dispensing a liquid eyewash. The apparatus is mounted on a wall and is intended to flush out foreign matter from a person's eyes in an emergency or other situation. The apparatus comprises a valve operable to release liquid solution into a spray means and the valve is operated by control means after a user correctly positions their head in relation to a guide means adjacent the spray means which results in actuation of the valve and subsequent release of a jet of the liquid via the spray means into the user's eyes.

12 Claims, 3 Drawing Figures

APPARATUS FOR DISPENSING A LIQUID EYEWASH

This invention relates to apparatus for dispensing liquid eyewash.

In many industrial situations accidents involving the entry of foreign matter into a person's eyes are common and it is important in this situation that such matter be flushed out of the victim's eyes as soon as possible. Most industrial plants have water supplied for various processes in the plant however, it is often the case that such water supplies are not immediately available for uses other than that for which they are intended and accordingly where an accident occurs to a person's eyes there can be some delay before the person's eyes can be cleansed with water.

It is an object of the present invention to provide an apparatus specifically designed for dispensing a liquid eyewash into a person's eyes in an emergency or in other situations where this is desired.

Further objects and advantages of the present invention will become apparent from the ensuing description of one embodiment thereof which is given by way of example.

According to a first aspect of the present invention, there is provided an apparatus for dispensing a liquid eyewash comprising a valve adapted to be connected to a liquid supply, spray means arranged to receive the liquid from the valve and to disperse the liquid in a jet into a person's eyes, guide means arranged adjacent the valve and spray means, said guide means being particularly intended to encourage a correct head position for a user of the apparatus in relation to the spray means, and control means associated with the guide means or operable separately from the guide means, said control means being arranged to operate the valve to release a liquid into the spray means.

An apparatus in accordance with the present invention can be wall mounted in a work place at a convenient height where a water supply is available and may include an appropriate plaque or the like instructing workers in its use.

The water supply to the apparatus may include arrangements whereby a special cleansing solution is siphoned from a reservoir therefore when the apparatus is operated such that the cleansing solution is mixed with water prior to entering the apparatus.

Figure 1:
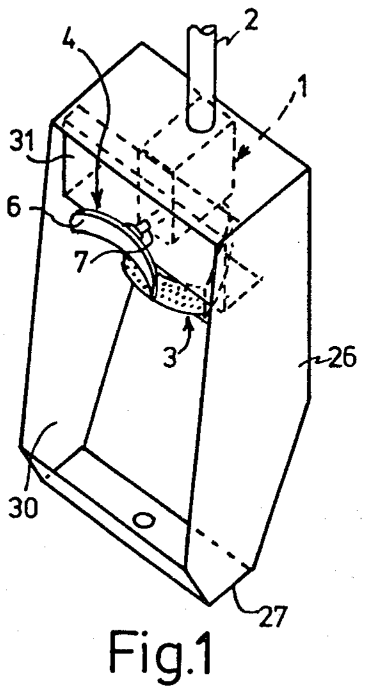
Figure 2:
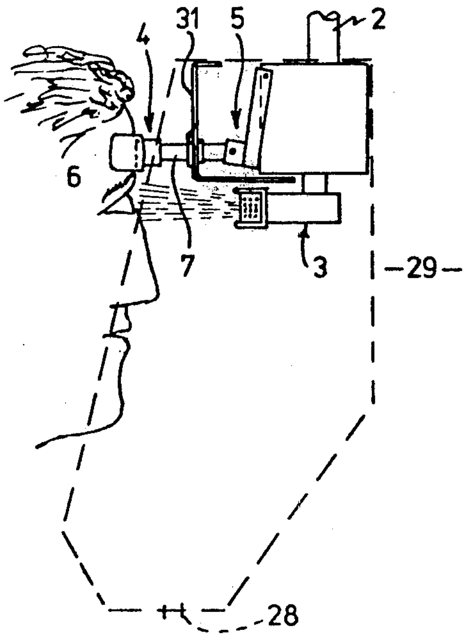
Figure 3:
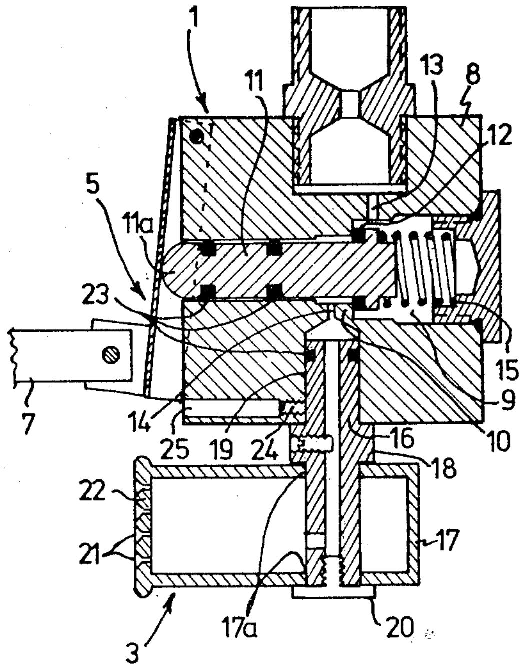

The valve controlling entry of liquid solution into the spray means of the apparatus can be a plunger operated valve associated with an electric solenoid or alternatively operation of the valve plunger can be effected mechanically. One embodiment of the present invention in which the valve plunger is mechanically operated will now be described with reference to the accompanying drawings in which:

FIG. 1: is a perspective view of one embodiment of an apparatus for dispensing a liquid eyewash solution in accordance with the present invention, and FIG. 2: is a side view of the apparatus of FIG. 1 with a housing therefor shown in dotted outline, and FIG. 3: is a cross-section of a typical valve and spray means for the apparatus illustrated by FIGS. 1 and 2.

With reference to the drawings, in the embodiment illustrated the apparatus for dispensing a liquid eyewash comprises a valve indicated by arrow 1 arranged to receive a liquid from a source (not shown) via a pipe 2, a spray means indicated by arrow 3, guide means indicated by arrow 4, arranged adjacent the valve 1 and spray means 3, said guide means 4 being particularly intended to encourage a correct head position for a user of the apparatus in relation to the spray means 3, and control means 5 associated with the guide means 4 arranged to operate the valve 1. In the embodiment illustrated the valve control is effected by mechanical means, in particular a pivotal lever arm which is arranged to operate a plunger of the valve 1.

In the embodiment illustrated the guide means 4 comprises a forehead rest portion 6 connected to a shaft 7 which is in turn pivotably connected to a pivotal lever arm as aforesaid. It should however be appreciated that the forehead rest 6 in the embodiment illustrated is a preferred form for the guide means and alternatives may be provided, for example a face mask or partial face mask (not shown) having openings through which a user can view the spray means 3 may be used in place of the forehead rest.

The valve 1 for the apparatus may comprise a valve body 8, a valve chamber 9 within the valve body including a valve seat 10, a spring loaded plunger 11 arranged coaxially within the valve chamber, said plunger having an elastomeric sealing means 12 arranged to coact with the valve seat 10 when the valve is closed and passages 13 and 14 are provided for entry to and egress from the valve chamber 9. The valve body 8 can be machined from a block of brass or another alloy suitable for the purpose and arrangements made for connection of the pipe 2 to the valve body, and connection of the spray means 3 of the apparatus. The passage 14 from the valve chamber 9 is sealed from the passage 13 to the valve chamber when the plunger 11 is in a closed position as is illustrated by the drawings.

The guide means 4 is pivotably connected to the control means 5, which is pivotably connected with respect to the body 8 of the valve, such that the control means is in contact with an extending end 11_a_ of the valve plunger 11. Thus, when a frontal push is applied to the forehead rest 6, the valve plunger 11 will become unseated and the valve will open allowing liquid to pass from the valve chamber 9 via passage 14 into the spray means 3. When the pressure is released from the forehead rest 6 the valve plunger 11 will return to its original position under the influence of its spring 15.

The spray means 3 is connected to the passage 14 by means of a coupling 16 which extends through a spraying head 17 of the spray means 3 and is arranged to release liquid into the spraying head. The coupling 16 can be fabricated from a tubular material having a boss 18 against which the spraying head 17 is restrained and one end of the coupling extends into an aperture 19 in the body 8 of the valve 1 coaxial with the passage 14 whilst the other end extends through apertures 17_a_ in opposite walls of the spraying head 17 and the head can be secured on the coupling by an end bolt 20.

The passages 13 and 14 to and from the valve chamber 9 are of a reduced cross-section designed to increase the velocity of liquid such that liquid released from the valve 1 will leave the spraying head via apertures 21 in a face plate 22 thereof in a jet designed to adequately cover the eye region of a user's head.

To prevent unwanted release of liquid from the valve 'O'-ring, seals 23 can be provided on the coupling and the plunger shafts, and the coupling may be locked in position by a locking key 24, access to which is gained through an aperture 25 in the valve body.

The apparatus illustrated in the drawings is mounted in a housing 26 having a base 27 arranged to collect liquid impinging from a user's face and piping 28 may be fitted to carry away such liquid. The housing which can be mounted on a wall 29 is provided with one open side 30 from which the spray means 3 and forehead rest 6 are directly accessible. The housing may also be provided with a front plate 31 which includes a guide aperture for the shaft 7 of the guide means 4. The housing 26 can be fabricated from steel or metal and coated with a protective and decorative paint or alternatively the housing may be moulded as a one piece unit from plastics material.

One embodiment of the present invention has been described by way of example only and it will be appreciated that modifications and additions thereto may be made without departing from the scope of the invention as defined in the appended claims.

I claim:

1. An apparatus for dispensing a liquid eyewash in an emergency to a person's eyes, comprising a supply of liquid, spray means arranged to disperse the liquid in a jet into said person's eyes, a valve connected to said supply of liquid and arranged to deliver the liquid to said spray means, guide means arranged adjacent the valve and said spray means, said guide means being arranged to provide a correct head position for said person in relation to the spray means, control means arranged to operate the valve to release a liquid into the spray means, wherein the valve is a plunger operated valve and the control means comprises a pivotal lever arm mechanism coupled to the plunger of the valve, and the said pivotal lever arm mechanism is arranged to move in response to pressure being applied to said guide means.

2. Apparatus as claimed in claim 1, wherein the guide means comprises a forehead rest pivotably connected to said pivotal lever arm, the arrangement being such that a person making contact with the forehead rest and applying pressure to the forehead rest with their forehead will cause a movement of the pivotal lever arm and corresponding movement of the plunger of the valve to release liquid eyewash to the spray means.

3. Apparatus as claimed in claim 2, wherein the valve comprises a valve body, a valve chamber within the valve body including a valve seat, a spring loaded valve plunger arranged coaxially within the valve chamber said plunger having an elastomeric sealing means arranged to coact with the valve seat when the valve is closed, and means of entry to and egress from the valve chamber.

4. Apparatus as claimed in claim 3, wherein the said means of egress from the valve chamber is sealed from the means of entry to the valve chamber when the valve is closed and the sealing means of the plunger is in contact with the valve seat within the chamber.

5. Apparatus as claimed in claim 4, wherein said means of entry to the valve chamber is arranged to be connected to a source of the liquid eyewash and includes a constricted passage to the valve chamber arranged to increase the flow rate of eyewash entering the valve chamber.

6. Apparatus as claimed in claim 5, wherein one end of the valve plunger extends proud of the valve body and a free part of the pivotal lever arm is constantly in contact with the extending end of the valve plunger.

7. Apparatus as claimed in claim 6, wherein the spray means comprises a spraying head joined to the valve by a coupling such that liquid can be received from the valve and thereafter dispersed in a jet pattern particularly intended to impinge on said person's eyes.

8. Apparatus as claimed in claim 1, including a housing having a base part arranged to collect liquid impinging from the face of said person.

9. Apparatus as claimed in claim 8, wherein the housing is provided with one open side and the spray means and the forehead rest are directly accessible from the open side.

10. Apparatus as claimed in claim 1, wherein the control means comprises an electrically operated solenoid having a plunger and valve wherein the plunger of the valve is connected to a plunger of the solenoid valve.

11. Apparatus as claimed in claim 8, wherein the housing is fabricated from steel or metal and coated with a protective and decorative paint or another anticorrosive material.

12. Apparatus as claimed in claim 8, wherein the housing is moulded as a one piece unit from plastics material.

* * * * *